(12) United States Patent
Amontov et al.

(10) Patent No.: US 8,268,563 B2
(45) Date of Patent: Sep. 18, 2012

(54) METHOD AND APPARATUS FOR SURFACE TREATMENT

(75) Inventors: Sergey Amontov, Heidelberg (DE); Emmanuel Delamarche, Thalwil (CH); Bruno Michel, Adliswil (CH)

(73) Assignee: International Business Machines Corporation, Armonk, NY (US)

( * ) Notice: Subject to any disclaimer, the term of this patent is extended or adjusted under 35 U.S.C. 154(b) by 742 days.

(21) Appl. No.: 10/539,726

(22) PCT Filed: Nov. 13, 2003

(86) PCT No.: PCT/IB03/05129
§ 371 (c)(1),
(2), (4) Date: Jul. 19, 2006

(87) PCT Pub. No.: WO2004/056470
PCT Pub. Date: Jul. 8, 2004

(65) Prior Publication Data
US 2007/0015153 A1    Jan. 18, 2007

(30) Foreign Application Priority Data

Dec. 20, 2002 (EP) .................................... 02028555

(51) Int. Cl.
*C12Q 1/68* (2006.01)
*C12P 19/34* (2006.01)
(52) U.S. Cl. ............... 435/6.12; 435/91.2; 435/91.21
(58) Field of Classification Search .................. None
See application file for complete search history.

(56) References Cited

U.S. PATENT DOCUMENTS

| | | | | |
|---|---|---|---|---|
| 5,512,131 A | * | 4/1996 | Kumar et al. | 438/738 |
| 5,686,271 A | * | 11/1997 | Mian et al. | 435/91.1 |
| 5,731,152 A | * | 3/1998 | Maracas et al. | 435/6 |
| 5,948,621 A | * | 9/1999 | Turner et al. | 435/6 |
| 6,180,239 B1 | | 1/2001 | Whitesides et al. | |
| 6,423,552 B1 | | 7/2002 | Lu et al. | |
| 6,432,360 B1 | * | 8/2002 | Church | 422/68.1 |
| 7,105,347 B2 | * | 9/2006 | Fang et al. | 435/455 |
| 2002/0071943 A1 | * | 6/2002 | Hawker et al. | 428/195 |
| 2003/0044781 A1 | * | 3/2003 | Korlach et al. | 435/6 |
| 2004/0203085 A1 | * | 10/2004 | Bernard et al. | 435/7.94 |

FOREIGN PATENT DOCUMENTS

| | | |
|---|---|---|
| WO | 9617959 A2 | 6/1996 |
| WO | WO9831839 | 7/1998 |
| WO | 9919341 A | 4/1999 |
| WO | 0070073 A1 | 11/2000 |
| WO | WO 200079023 A1 * | 12/2000 |

OTHER PUBLICATIONS

Kumar et al. Features of gold having micrometer to centimeter dimensions can be formed through a combination of stamping with an elastomeric stamp and an alkanethiol "ink" followed by chemical etching. Applied Physics Letters (1993) 63(14): 2002-2004.*
Richter et al. Nanoscale Palladium Metallization of DNA. Advanced Materials (2000) 12(7): 507-510.*
Bernard et al., Microcontact Printing of Proteins, Adv. Mater. 2000, 12, No. 14, Jul. 19, pp. 1067-1070.
Ramsay, Graham. DNA chips: State-of-the-art. Nature Biotechnology. vol. 16, Jan. 1998, pp. 40-44.
Xia et al., Soft Lithography, Angew. Chem. Int. Ed. 1998, 37, pp. 550-575.
Kane et al., "Patterning proteins and cells using soft lithography". Biomaterials 20, pp. 2363-2376 (1999).

* cited by examiner

*Primary Examiner* — Angela M Bertagna

(57) ABSTRACT

A method for producing a monolayer of molecules on a surface comprises: loading a stamp with seed molecules; transferring seed molecules from the stamp to the surface; and, amplifying the seed molecules via an amplifying reaction to produce the monolayer. The method permit generation of complete monolayers from incomplete or sparse monolayers initially printed on the surface.

16 Claims, 8 Drawing Sheets

Fig. 3G

-NH 5'-EEE EEE EEE EEE EEE SSS SSS SSS SSS SSS SSS SSS SSS SSS BBB BBB BBB BBB BBB AZ 3'

-NH 5'-PPP PPP PPP PPP PPP TTT TTT TTT TTT TTT TTT TTT TTT TTT TTT RRR RRR RRR RRR RRR AZ 3'

-NH 5'-EEE EEE EEE EEE EEE SSS SSS SSS SSS SSS SSS SSS SSS SSS BBB BBB BBB BBB BBB AZ 3'

-NH 5'-PPP PPP PPP PPP PPP TTT TTT TTT TTT TTT TTT TTT TTT TTT TTT RRR RRR RRR RRR RRR AZ 3'

-NH 5'-EEE EEE EEE EEE EEE SSS SSS SSS SSS SSS SSS SSS SSS SSS BBB BBB BBB BBB BBB AZ 3'

-NH 5'-PPP PPP PPP PPP PPP TTT TTT TTT TTT TTT TTT TTT TTT TTT TTT RRR RRR RRR RRR RRR AZ 3'

-NH 5'-PPP PPP PPP PPP PPP TTT TTT TTT TTT TTT TTT TTT TTT TTT TTT RRR RRR RRR RRR RRR AZ 3'

-NH 5'-PPP PPP PPP PPP PPP TTT TTT TTT TTT TTT TTT TTT TTT TTT TTT RRR RRR RRR RRR RRR AZ 3'

-NH 5'-PPP PPP PPP PPP PPP TTT TTT TTT TTT TTT TTT TTT TTT TTT TTT RRR RRR RRR RRR RRR AZ 3'

1

METHOD AND APPARATUS FOR SURFACE TREATMENT

CROSS REFERENCE and PRIORITY

This application filed under 35 USC 371, is cross-referenced with, and claims priority from, International Patent Application PCT/IB2003/005129 filed on Nov. 13, 2003, and published in English with Publication No. WO 2004/056470 A1 on Jul. 8, 2004, under PCT article 21(2). which in turn claims priority of European Application No. 02028555.7, filed on Dec. 20, 2002.

FIELD OF THE INVENTION

The present invention generally relates to surface treatment and particularly relates to methods for coating surface areas with molecular monolayers.

BACKGROUND OF THE INVENTION

Molecular monolayers on surfaces are useful in many applications, including controlling corrosion, wetting or adhesion properties of a surface, performing heterogeneous catalysis, extracting or purifying analytes from solutions, and for producing biosensors or biochips.

A conventional process for depositing a molecules on a substrate surface involves immersing the surface in a solution having an excess of molecules for forming a self-completing monolayer on the surface. A disadvantage of conventional immersion based monolayer processing techniques is that they do not allow fine patterning. In addition, they are complex, expensive, slow, and inaccurate both chemically and geometrically. Conventional manufacture of DNA functionalized biochips involves spotting with DNA templates. Surface tension in the spot is relied upon to define spot geometry. Drying effects quickly change concentration in the spot and render control difficult.

Another conventional process for depositing molecules on a surface involves printing the monolayer on the surface from a stamp such as a stamp made in poly dimethyl siloxane (PDMS). Printing allows patterning of the surface with minute amounts of molecules. However, there is a variable transfer associated with such printing. Coverage at a given spot on the surface depends on both inking density and printing efficiency. This is particularly problematical where molecules can only be placed as a monolayer on the stamp in, for example, printing of catalysts or biological molecules. Here, contrast between a passive and a functional surface is provided by the presence or absence of a single molecule. A single missing molecule produces a defect. Conventionally, transfer of monolayers from a stamp to a surface is not free of defects and transfer ratios vary from one print cycle to the next. This is undesirable for mass production environments. See, for example, A. Bernard et al., "*Microcontact Printing of Proteins*", *Adv. Mater.* 2000 (12), 1067 (2000)

So-called biochip or micro array technology is increasingly important in applications such as genetic analysis, including examination of gene activity and identification of gene mutations. Genetic information can be used to improve drug screening, diagnostics, medication, and identification. A typical biochip for such an application comprises a miniature array of gene fragments or proteins attached to a glass surface. Typically a hybridization reaction between sequences on the surface of such biochips and a fluorescent sample is used for the analysis. Following hybridization, biochips are typically read with fluorescence detectors, permitting the fluorescent intensity of spots on the surface to be quantified. Protein markers, viruses, and protein expression profiles can be similarly detected via protein specific capture agents. Conventional methods for patterning biological molecules on biochips are described in M. Schena, "*Micro array Biochip Technology*", Eaton Publishing, Natick Mass., (2000) and G. Ramsay, "*DNA chips: State of the Art*", Nature Biotech, 16, 40 (1998). Conventional methods include sequential and parallel patterning techniques. The sequential techniques serially address spots on the surface. These techniques include: pipetting; capillary printing; ink jet printing; and, pin spotting. The parallel techniques pattern multiple areas of molecules onto the surface simultaneously. These techniques include: microfluidic network delivery; capillary array printing; and, microcontact printing. Microcontact printing involves inking a patterned stamp. Such inking may be performed via a microfluidic network.

Deoxyribonucleic acid (DNA) may be applied to a biochip surface for some applications. The information encoded in DNA establishes and maintains cellular and biochemical functions of an organism. In most organisms, DNA is an extended double stranded polymer. The sequence of deoxyribonucleotides of one DNA is complementary to those of the other strand. This enables new DNA molecules to be synthesized with the same linear array of deoxyribonucleotides in each strand as an original DNA molecule. This process is generally referred to as DNA replication. The DNA code is made up from four bases: adenine (A), guanine (G), cytosine (C), and thymine (T). A nucleotide consists of one of the four organic bases, a five carbon sugar (pentose), and a phosphate group. The phosphate group and organic base are attached to the 5' carbon and 1' carbon atoms of the sugar moiety, respectively. The sugar of DNA is 2' deoxyribose because it has a hydroxyl group only on the 3' carbon. The nucleotides of DNA are joined by phoshodiester bonds with the phosphate group of the 5' carbon of one nucleotide linked to the 3' OH of the deoxyribose of the sugar of the adjacent nucleotide. A polynucleotide thus has a 3' OH at one end (3'end) and a 5' phosphate group at the other end (5'end). DNA forms a double stranded helix with bases A pairing with T and bases G pairing with C via two and three hydrogen bonds, respectively. The two strands of a duplex DNA run in opposite directions, by convention double stranded DNAs are always written with the 5' end of the upper strand on the left. During the enzymatic replication process, the phosphate of the added nucleotide is linked to the 3' OH of the existing sequence. Thus, DNA is always replicated from 5' to 3' direction as described in B. R. Glick, et al., "*Molecular Biotechnology: Principles and Applications of Recombinant DNA*", American Society for Microbiology, Washington 1998.

Manufacture of DNA functionalized biochips conventionally involves sequential inking of spots with a different DNA template to from DNA targets. This is complex, slow and thus expensive process.

Conventionally, gene analysis was performed by hybridization of labeled probes to the DNA targets that were passively adsorbed to support surfaces such as nitrocellulose, nylon membranes, or lysine coated glass slides. Covalent linkage of DNA to the surface provides stable attachment under hybridization conditions. DNA oligomers can be attached or synthesized in situ from either the 3'-end or the 5'-end. Processes for attaching 5'-end oligonucleotides to glass include: an epoxy opening reaction on epoxy silane derivatized glass such as described in K. L. Beattie et al. *Clin. Chem.* 41, 700-706 (1995); 5'-succinylated target oligonucleotides immobilized onto amino derivatized glass such as described in Joos, B. et al., *Anal. Biochem.* 247, 96-101

(1997); and, 5'-disulfide modified oligonucleotides bound via disulfide bonds onto thiol derivatized glass such as described in Rogers, Y. H. et al., *Anal. Biochem.* 266, 23-30 (1999). Other processes use cross linkers such as pehyldiisocyanate, maleic anhydride, or carbodiimides and are described, for example, in Chrisey, L. A. et al., *Nucleic Acids Res.* 24, 3031-3039 (1996), O'Donnell, M. J. et al., *Anal. Chem.* 69, 2438-2443 (1997), Chee, M., et al., "*Accessing genetic information with high-density DNA arrays*", *Science* 274, 610-614 (1996). An overview of attachment chemistries is published in G. T. Hermanson, "*Bioconiugate Techniques*", Academic Press, San Diego, 1996. Reproducible chemisorption of oligomers in particular are described in: Adessi, C. et al. *Nucleic Acid Res.* 28 (e87) 1-8 (2000); Kawashima, E., et al., "Method of nucleic acid amplification", WO 98/44151; and, Adessi, C., et al., "Methods of nucleic acid amplification and sequencing", WO 00/18957.

The polymerase chain reaction (PCR) is an in vitro technique permitting exponential amplification of a specific ribonucleic acid (RNA) or deoxyribonucleic acid (DNA) region lying between two regions of known DNA sequence. Conventional applications of PCR include: gene characterization; cloning; DNA diagnostics for pathogen detection; identifying mutations responsible for inherited diseases; and, DNA fingerprinting. PCR amplification is achieved via oligonucleotide primers known as ampliprimers. These are short, single stranded DNA molecules which are complementary to the ends of a defined sequence of DNA template. The primers are extended in 3' directions on single stranded denatured DNA by a thermostable DNA polymerase in the presence of deoxynucleoside triphosphates (dNTPs) under suitable reaction conditions. Strand synthesis can be repeated by heat denaturation of the double stranded DNA, annealing of primers by cooling the mixture and primer extension by DNA polymerase at a temperature suitable for enzyme reaction. Each repetition of strand synthesis comprises a cycle of amplification. Each new DNA strand synthesized becomes a template for any further cycle of amplification. The amplified target DNA is thus amplified exponentially. For further information relating to PCR, see C. R. Newton et al., "*PCR*", Bios Scientific Publishers, Oxon, U. K. 2000, E. Southern et al. "*Molecular Interactions on Microarrays*", *Nature Genetics* 21, 5 (1999); U. Maskos et al., "*Oligonucleotide hybridizations on glass supports*" *Nucleic Acid Res.* 20(7), 1679-1684 (1992); Z. Guo et al., "*Direct Fluorescence Analysis of Genetic Polymorphisms by Hybridization with Oligonucleotide Arrays on Glass Supports*" *Nucleic Acid Res.* 22 (24), 5456-5465 (1994); J. Lamture et al., "*Direct Fluorescence of Nucleic Acid Hybridization on the Surface of a Charge Coupled Device*" *Nucleic Acid Res.* 22(11), 2121-2125 (1994); M. Sjoeroos et al., "*Solid-Phase PCR with Hybridization and Time-Resolved Fluorometry for Detection of HLA-B27*", *Clinical Chem.* 47(3), 498 (2001).

SUMMARY OF THE INVENTION

All of the above mentioned methods to pattern monolayers on surfaces have strong limits and patterns cannot be optimized after the patterning step. It would be desirable to solve such problems and have printing processes that consume less ink, thus requiring less frequent inking and allowing faster operation due to shorter contact times being needed for molecular transfer.

In accordance with the present invention, there is now provided a method for producing a monolayer of molecules on a surface, the method comprising: loading a stamp with seed molecules; transferring seed molecules from the stamp to the surface; and, amplifying the seed molecules via an amplifying reaction to produce the monolayer.

In a preferred embodiment of the present invention, the transferring comprises transferring a fraction of the seed molecules loaded on stamp to the surface. Preferably, this is achieved by the transferring comprising adsorbing the seed molecules to the stamp and adsorbing the seed molecules to the surface, the adsorption of the seed molecules to the stamp being stronger than the adsorption of the seed molecules to the molecules to the surface. The amplifying may comprises an in vitro translation system to produce a monolayer of protein. The seed molecules may comprise a catalyst center for electroless deposition. The method may include binding a catalyst to the seed molecules for electroless deposition. In a preferred application of the present invention, the monolayer protects the surface from etchants. In a particularly preferred embodiment of the present invention, the monolayer comprises DNA. Preferred examples of the method further comprise repeating the transferring and amplifying on plural surfaces before reloading the stamp with seed molecules. The present invention also extends to a biosensor comprising surface treated with a method as herein before described.

In a preferred embodiment of the present invention, there is provided a surface treatment method comprising: transferring an incomplete molecular monolayer to the surface; and, using the incomplete layer as the basis for completing the monolayer by an amplifying reaction. The amplifying reaction, which may involve immersion of the surface in solution, is preferably selective of predefined zones of the surface to prevent unwanted surface coverage. Reaction induced enlargement of the zones is preferably limited to avoid excessive distortion of surface patterning. In particularly preferred embodiments of the present invention, the process is self completing, thus solving the aforementioned problem of variable transfer ratio. This allows more prints between re-inking, to conserve ink, and to print faster, without significantly distorting surface patterning. A subsequent reaction may convert printed species to different species which may be unprintable by other techniques. The present invention is particularly although not exclusively useful for amplifying sparse monolayers such as sparse DNA monolayers.

Examples of amplification schemes for completing the monolayer include linear amplification, exponential amplification such as PCR amplification, and directional amplification. Advantageously, such schemes are generally independent from patterning methods. Linear amplification is useful for completing defective monolayers. However, exponential amplification is preferred for building monolayers from sparse molecules because it is relatively fast in execution. Directional amplification, intrinsically directional or dependent on application of an external field, permits formation of nanostructures bridging small gaps. Such amplification schemes can be implemented in inorganic, organic, and biological systems. Each of these schemes will be described in further detail shortly. Advantageously, these schemes can be implemented using DNA oligomers. DNA may be detected and amplified using a copying process such as PCR. It is desirable to amplify multiple DNAs in parallel in the interests of mass production. In a particularly preferred embodiment of the present invention, parallel amplification is combined with soft lithography printing to provide mass production simplicity and reduced cost. Specifically, oligomers are patterned onto a surface via a stamp. The patterning quality depends on the efficiency of chemisorption of capture oligomers on the stamp and of primer oligomers on the surface. The template oligomer preferably has a controlled but reversible hybridization with stronger bonding to the capture oligomer on the stamp than to the primer oligomer on the surface. Alternatively, capturing of templates on the stamp can be achieved nonspecifically using polylysine. For efficient surface bound PCR, oligomers preferably have spacer sequences (9 T), are preferably bound on a biocompatible spacer layer (PEG), and preferably have a thermostable covalent crosslink retaining them on the surface during thermal cycling.

In a particularly preferred embodiment of the present invention, DNA printed from a spot feature on a stamp is reduced in amount for each printing cycle. This allows repetitive use of the stamp without re-inking. The number of printing cycles possible is proportional to the inverse fraction transferred during each printing cycle. Printing of less than 0.1% per printing cycle for example allows the reuse of the stamp around 1000 times before replacement or re-inking. Printing of more than 25 DNA molecules per square micrometer is possible. This is sufficient for use in PCR amplification using surface bound primers. PCR replication with a common primer region and a variable sequence allows replication of many thousands of different molecules in parallel.

BRIEF DESCRIPTION OF THE DRAWINGS

In a preferred embodiment of the present invention, the seed molecules are directionally amplified to form conductive structures. Directionally amplified seed molecules may be electroplated with a metal. The directional amplification may be controlled by the geometry of the seed molecule. Alternatively, the directional amplification may be controlled by application of an external force. Examples of external forces applicable include: electrical force; magnetic force; and, hydrodynamic force.

Preferred embodiments of the present invention will now be described, by way of example only, with reference to the accompanying drawings, in which:

FIGS. 3A to 3H are block diagrams of steps in a method for PCR surface primer amplification;

DETAILED DESCRIPTION OF THE PREFERRED EMBODIMENTS

Figure 1:
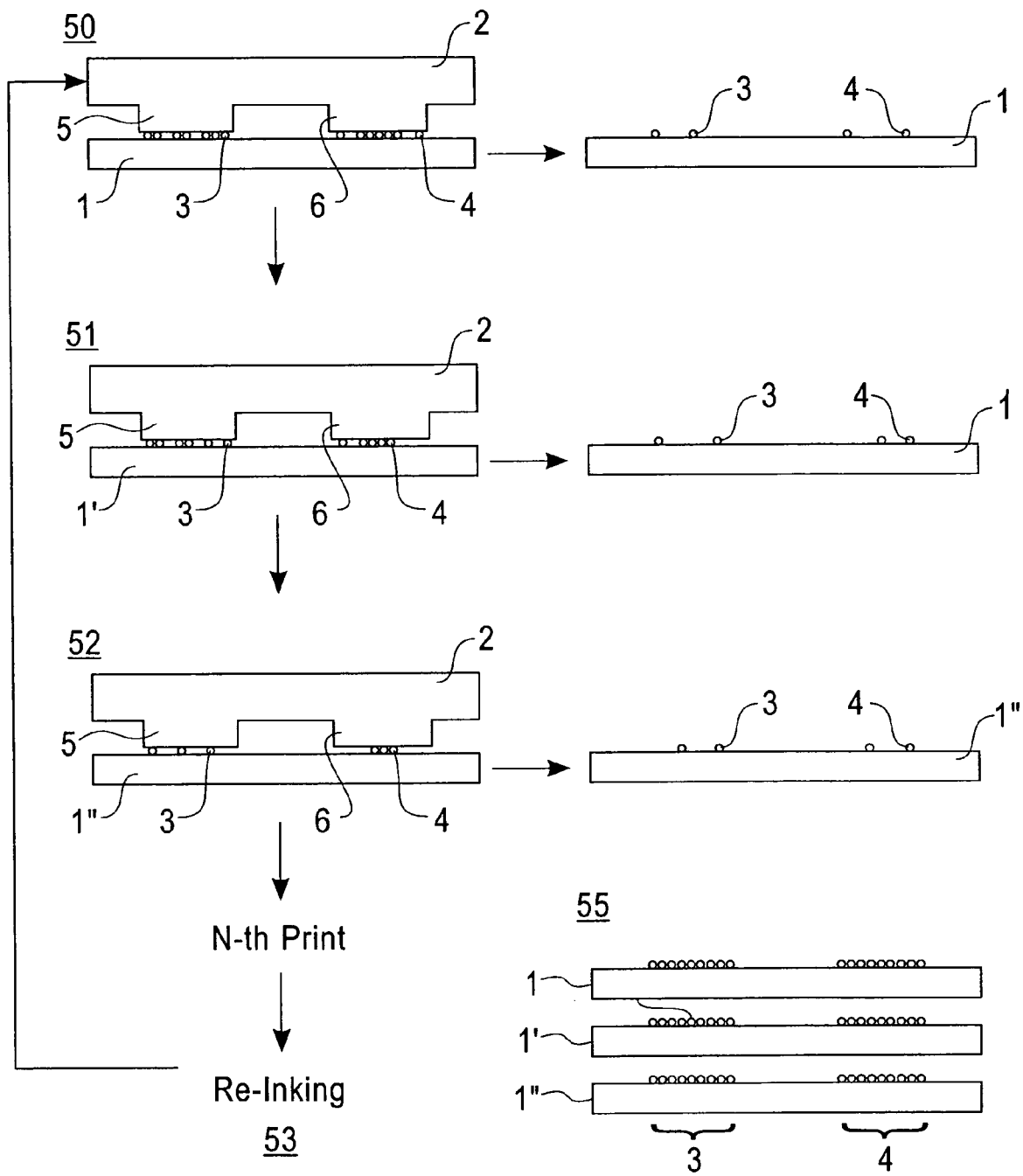
FIG. 1 is a block diagram of a surface treatment process embodying the present invention.

Referring first to FIG. 1, in a preferred embodiment of the present invention, there is provided a method for forming a molecular monolayer on surface 1. The method comprises transferring a seed layer of molecules 3,4 to the surface via a stamp 2. The seed layer comprises a molecular monolayer sparsely populated with molecules 3,4. The seed layer deposited on the surface 1 is then grown by an amplifying reaction to complete the monolayer on the surface 1. Different types of molecules 3,4 may be disposed on different active zones 5,6 of the stamp 2. This technique solves the problem of incomplete molecular transfer from the stamp 2 by transferring at least a catalytic amount of molecules and thereafter amplifying the molecules printed on the surface 1 to saturation density. In detail, at step 50, the stamp 2, partially inked with molecules 3,4, is brought into contact with the surface 1. In this example, a first group of molecules 3 is inked onto feature 5 of the stamp 2 and a second group of molecules 4 is inked onto feature 6 of the stamp 6. Molecules 3 and 4 may be of different species. The stamp 2 transfers a fraction of the inked molecules 3,4 to the surface 1. At step 55, an amplifying reaction is performed. The amplifying reaction amplifies the printed molecules 3,4 to produce complete monolayers. Meanwhile, at step 51, the stamp 2 is reused to print another fraction of the remaining molecules 3,4 onto another surface 1'. Again, at step 55, the amplifying reaction amplifies the molecules 3,4 printed on the other surface 1' to produce complete monolayers. Similarly, at step 52, the stamp 2 is reused again to print yet another fraction of the remaining molecules 3,4 onto yet another surface 1". Again at step 55, the amplifying reaction amplifies the molecules printed on the surface 1" to produce complete monolayers. In a batch process additional surfaces can be similarly treated until, on the Nth print, there are no molecules 3,4 remaining on the stamp 2. At step 53, the stamp can then be reinked and the process repeated. The amplifying reaction at step 55 may comprise an in vitro translation system to produce a monolayer of protein. The seed molecules 3,4 may comprise a catalyst center for electroless deposition. A catalyst may be bound to the molecules 3,4 for electroless deposition. In a preferred application of the present invention, the monolayers protect the surface 1 from etchants. The molecules 3,4 may be DNA oligomers.

Amplifying of printable DNA molecules may also be done on the stamp 2 followed by transfer of the complete monolayer. This method is however disadvantageous because a lithographic stamp is a costly and thermally sensitive article. Economically, this method is not useful because it occupies the stamp for at least one cycle of amplification. When the amplification in done on substrate surfaces, it can be done in a batch process, involving multiple substrates printed by the same stamp.

Figure 2A:
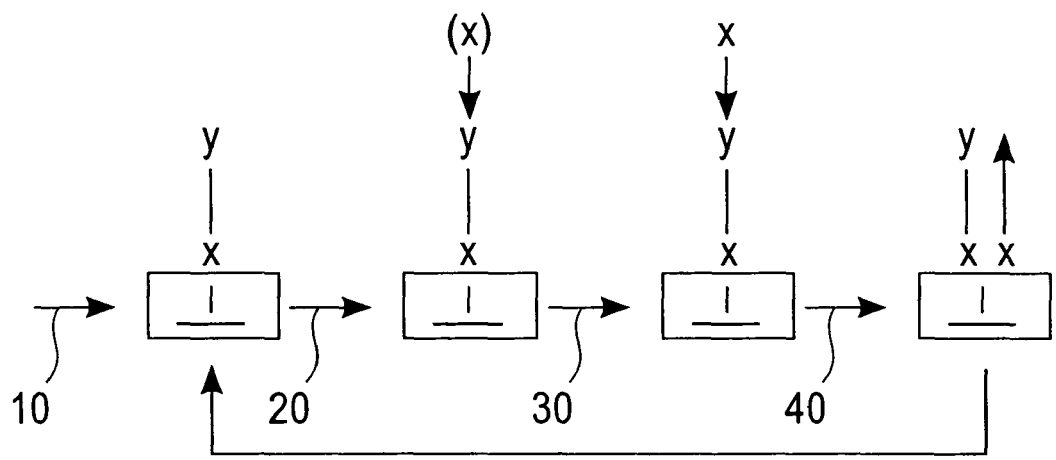
FIG. 2A is a block diagram of linear amplification.

The amplifying reaction may be a linear amplification reaction, an exponential amplification reaction, or a directional amplification reaction. Other amplifying reaction may be possible. An example of linear amplification of an incomplete printed monolayer of molecules having headgroup X, a backbone, and tailgroup Y will now be described with reference to FIG. 2A. Group Y provides an anchor for the V part of a molecule that also has a group X binding to the surface 1. The reaction stops at the edge of the print, where X and V have insufficient affinity for the surface 1. In detail, at step 10, the incomplete monolayer of the X-Y molecules is printed on the surface 1. At step 20, the tail group Y binds to the surface 1 from solution a molecule having a V function, a backbone and a precursor chemisorbing group (X). At step 30, the chemisorbing group (X) is deprotected to expose X. At step 40, this leads to chemisorption of the bound molecule to the surface. Chemisorption occurs only if the surface 1 is not already covered. The binding, deprotecting and amplifying steps can be repeated to progressively amplify the initial print until the surface 1 is covered. This process is thus self-limiting. It stops when the monolayer is complete or when no empty sites on the surface 1 remain in reach of molecules bound to Y tails. If the monolayer is patterned, the process produces negligible spreading, thus maintaining resolution and the maximum of molecules added after m amplification cycles is m, corresponding to linear amplification.

Figure 2B:
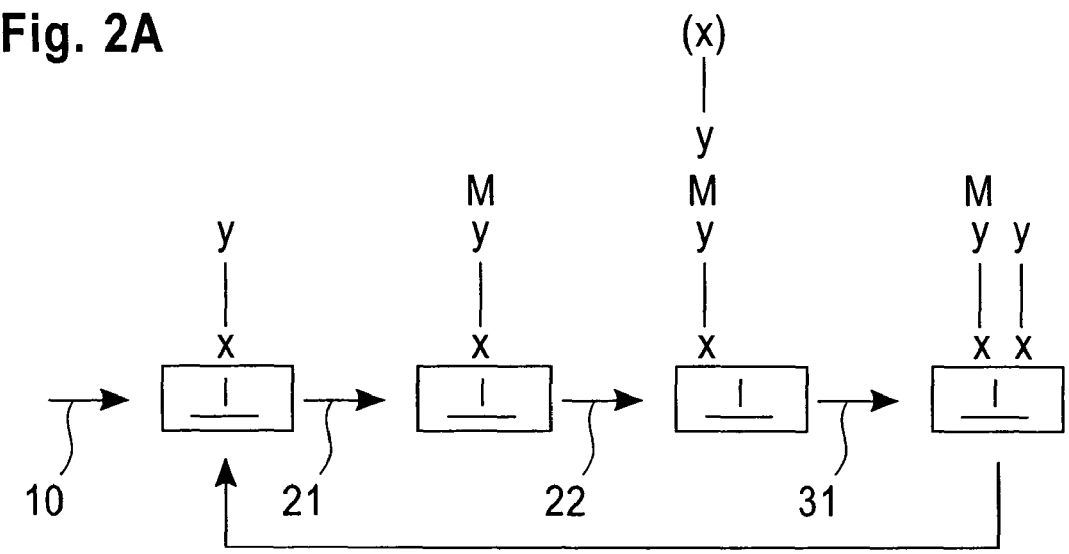
FIG. 2B is a block diagram of exponential amplification.

Referring now to FIG. 2B, in an example of exponential amplification of an incomplete printed monolayer comprising molecules having headgroup X and tailgroup Y, a complex or mediator M allows binding of more molecules and promotes adsorption to the surface 1. Since the newly bound tail groups Y also act as binding sites for M, the number of molecules N increases at $2^N$. This process is similar to linear amplification. However, after the printing step 10, Y tails are complexed at step 21 with an atom or molecule M. At step 22, a second molecule having a headgroup (X) and tail group Y is bound to M. At step 31, the headgroup (X) of the second molecule is deprotected to X and chemisorbed to the surface 1. Amplification thereafter proceeds by repeating the first binding step 21, second binding step 22, and deprotection step 31. Every molecule deposited on the surface can serve to amplify the monolayer further.

Figure 2C:
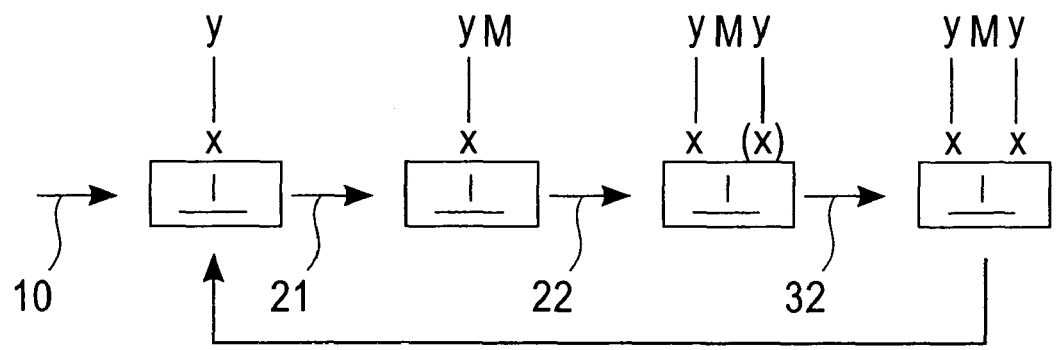
FIG. 2C is a block diagram of directional amplification.

Directional amplification will now be described with reference to FIG. 2C. Direction amplification is similar or faster than linear amplification except that now, at step 32, the second binding molecule is chemisorbed onto the surface in a directional manner which is set by the geometry of the complex YMY. Seed molecules may be directionally amplified to form conductive structures. Directionally amplified seed molecules may be electroplated with a metal. The directional amplification may be controlled by the geometry of the seed molecule. Alternatively, the directional amplification may be controlled by application of an external force. Examples of external forces applicable include: electrical force; magnetic force; and, hydrodynamic force.

The three amplification schemes can be used to coat surfaces with DNA oligomers. Exponential amplification in particular is especially useful for derivating surfaces with DNA. PCR amplification is an example of an exponential amplification scheme. In a preferred embodiment of the present invention, DNA molecules are sparsely printed from a stamp onto a surface as herein before described with reference to FIG. 1 and then amplified to produce a complete monolayers via solid phase PCR. The three amplification schemes herein before described are also suited to amplify monolayers in general and in particular printed monolayers or may be used to grow molecular structures along preferential directions of a surface to make nanostructures, for example.

Figure 3A:
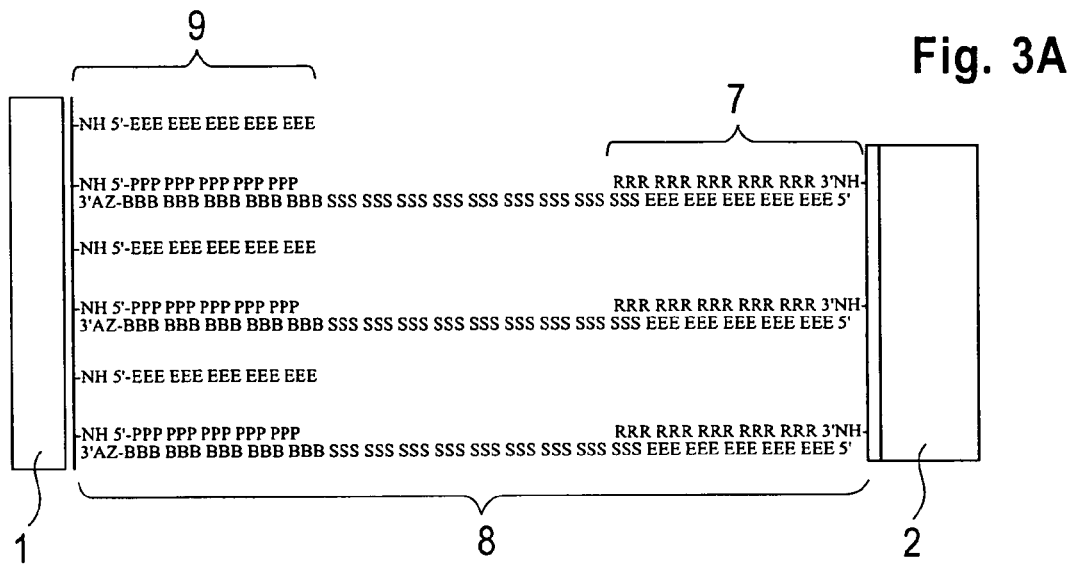
Figure 3B:
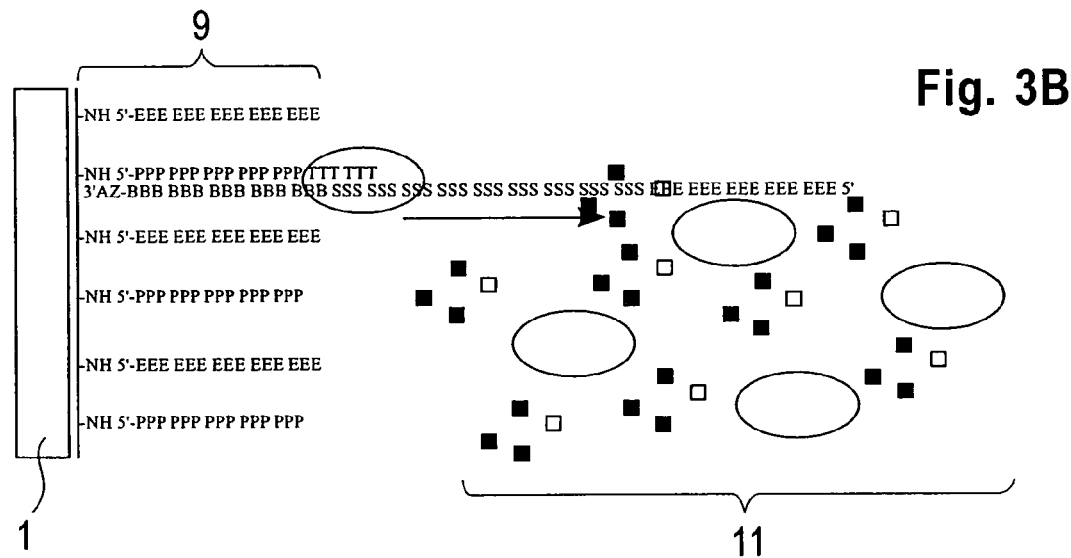
Figure 3C:
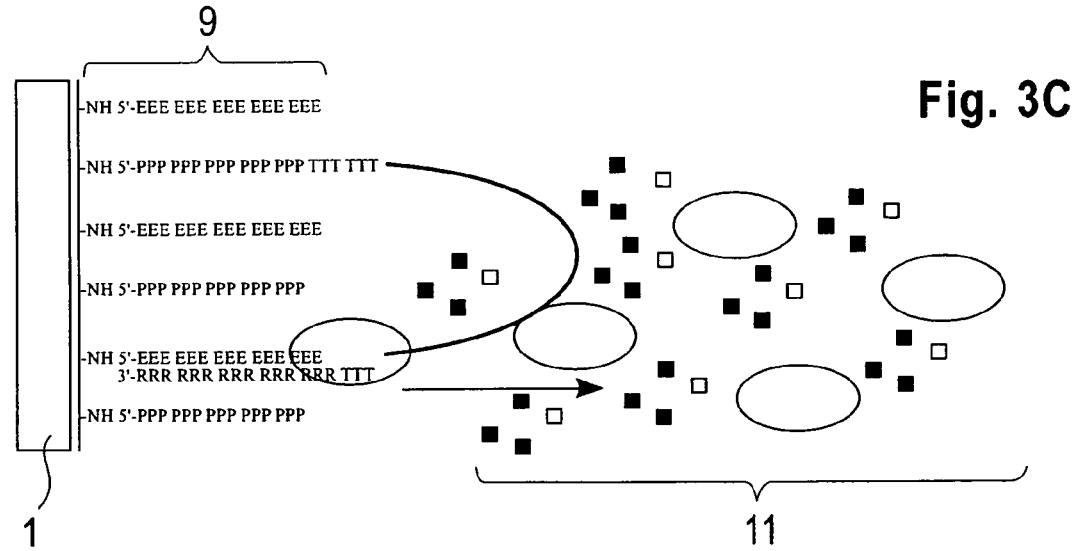
Figure 3D:
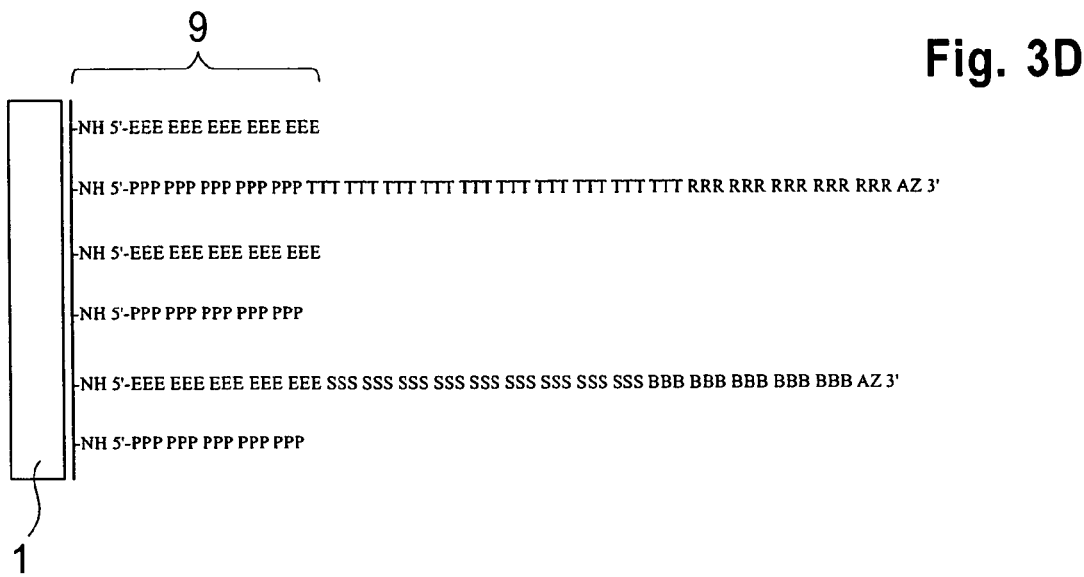
Figure 3E:
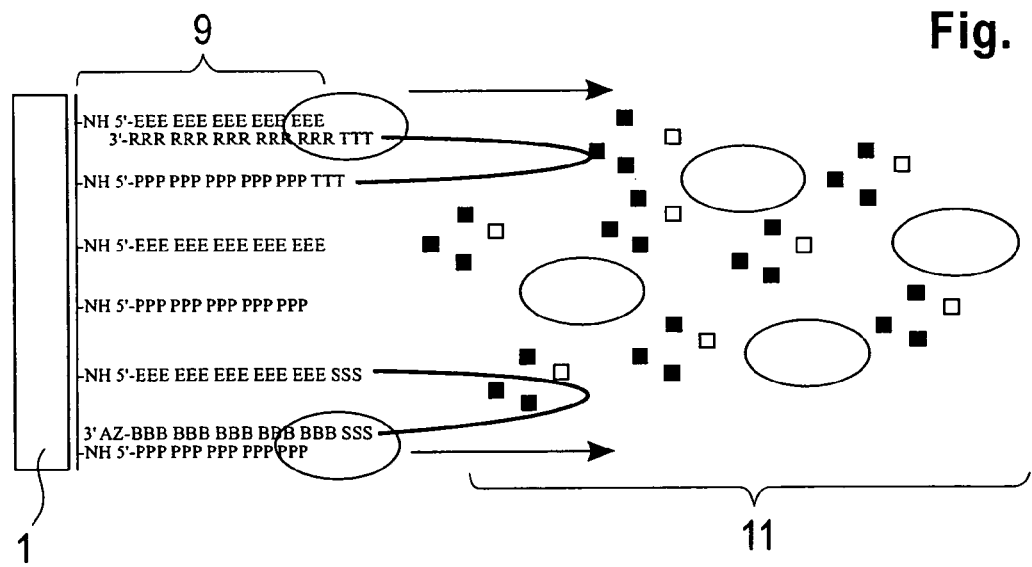
Figure 3F:
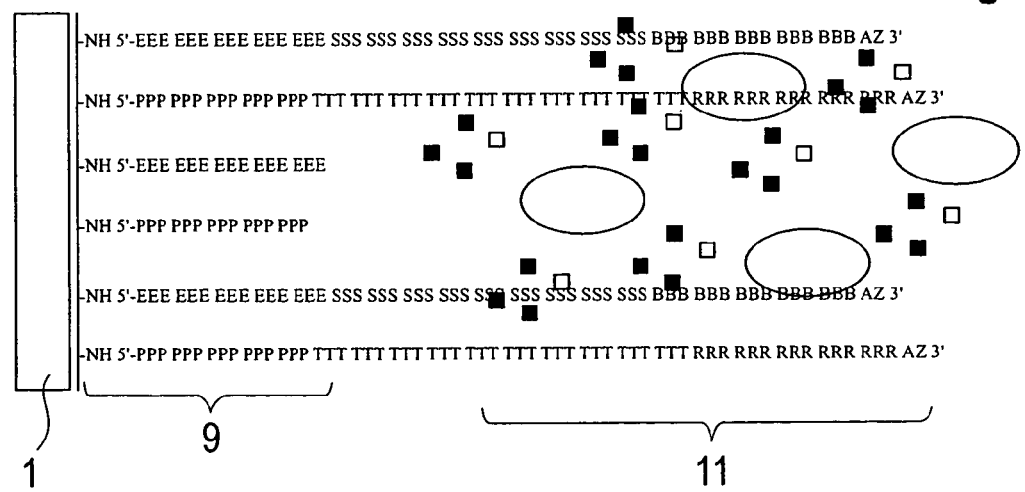

A method for surface primer PCR replication will now be described with reference to FIGS. 3A to 3H. Referring to FIG. 3A, template oligomers 8 are initially held on the stamp 2 by capture oligomers 7. The stamp 2 is then brought into contact with the surface on which first and second primer oligomers 9 are immobilized. A fraction of the templates 8 hybridize with the primers 9 and are thus transferred from the stamp 2 to the surface 1. Turning to FIG. 3B, a PCR mix 11 comprising DNA polymerase and the four PCR nucleotides (dNTPs) in a buffer solution of phosphate buffered saline (PBS) is then added. Each immobilized primer hybridized to a DNA template is amplified by DNA polymerase in the PCR mix 11 to full length on the surface 1. This produces a synthesized complementary or duplex DNA strand. Referring to FIG. 3C, heat is now applied. The duplex DNA strand melts and rehybridizes with another primer 9 on the surface 1 to produce a bridged molecule. Referring now to FIG. 3D, further application of heat melts the bridged molecule. Two duplex DNA strands bound to the surface 1 are thus produced. Referring now to FIG. 3E, temperature is reduced. Each of the two duplex strands rehybridizes with a matching primer 9 and the primers 9 are extended. Two bridged molecules are thus produced. Referring now to FIG. 3F, further application of heat melts the bridged molecules. Now four duplex DNA strands are bound to the surface 1. Referring now to FIG. 3G, the melting and rehybridizing steps are repeated until all primers 9 are elongated. Turning to FIG. 3H, the complementary molecules are then cleaved from the surface 1 chemically or via a restriction enzyme.

Figure 4A:
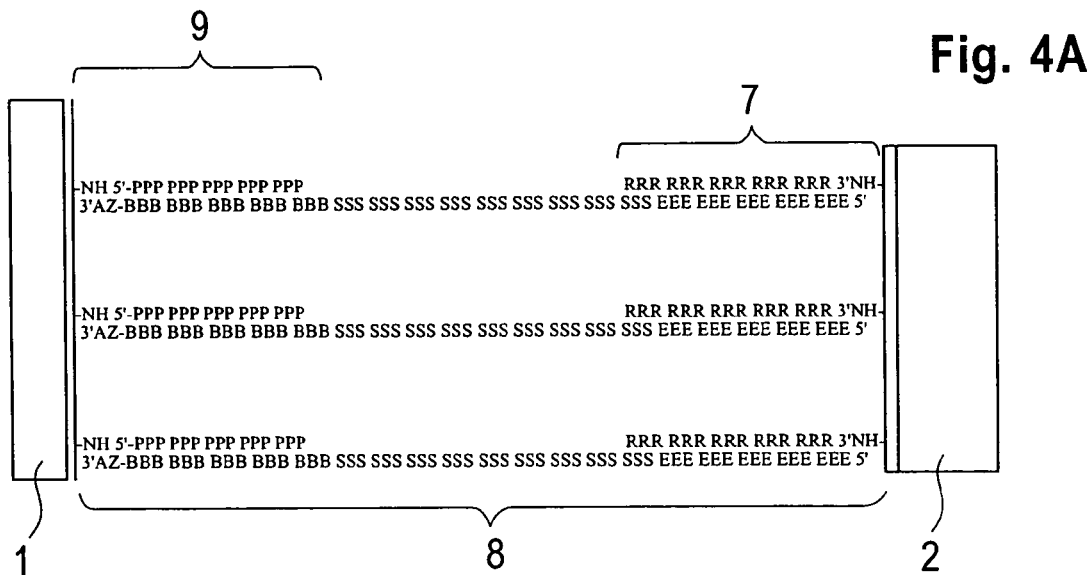
FIGS. 4A to 4E are block diagrams of steps in a method for PCR soluble primer amplification; and, FIGS. 5A to 5E are cross sectional view of a stamping operation for a surface treatment methods embodying the present invention.
Figure 4B:
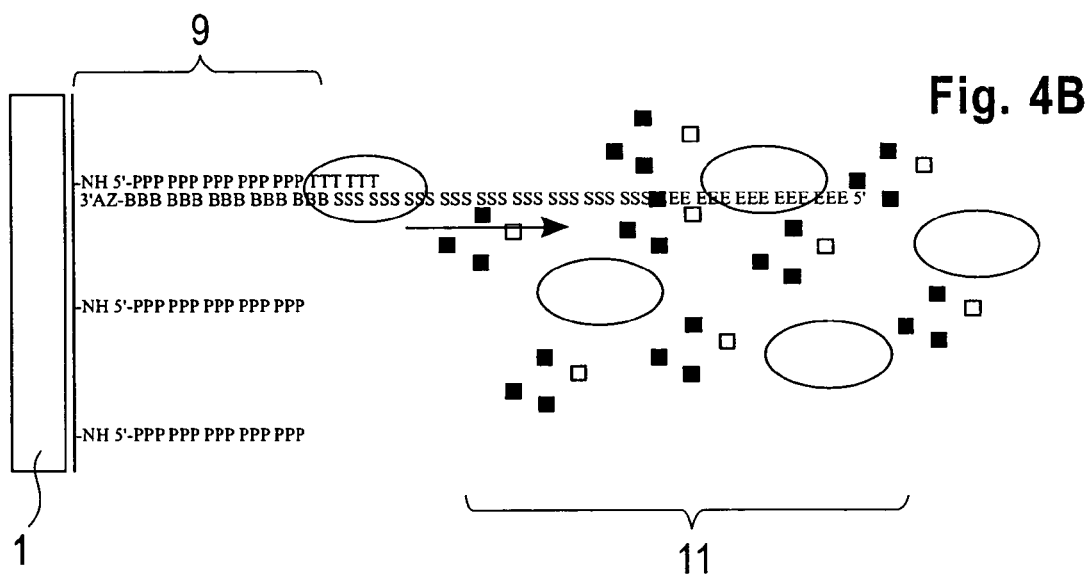
Figure 4C:
Figure 4D:
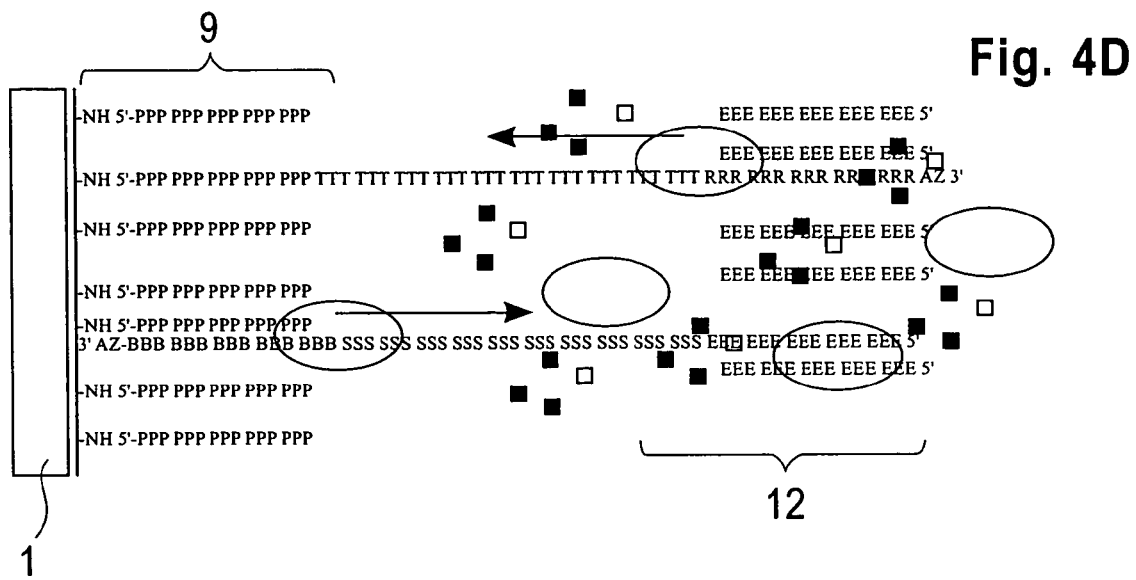
Figure 4E:
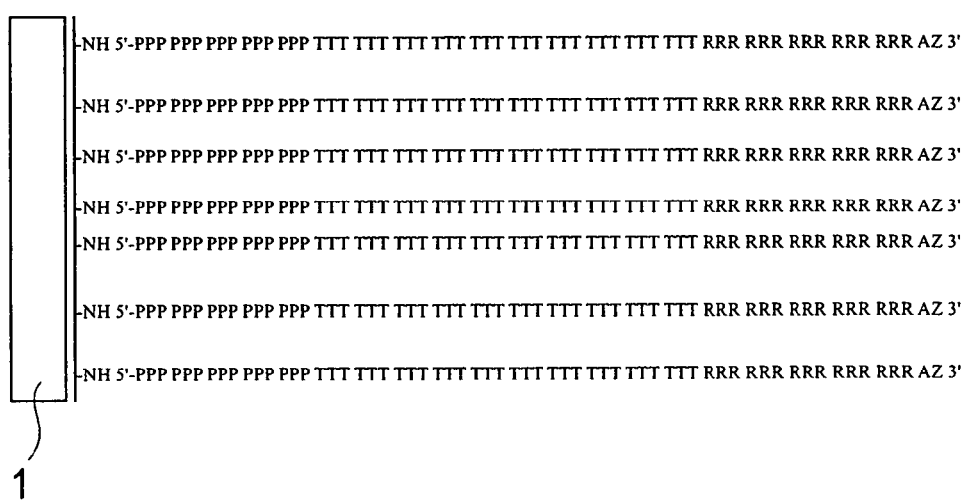
Figure 5A:
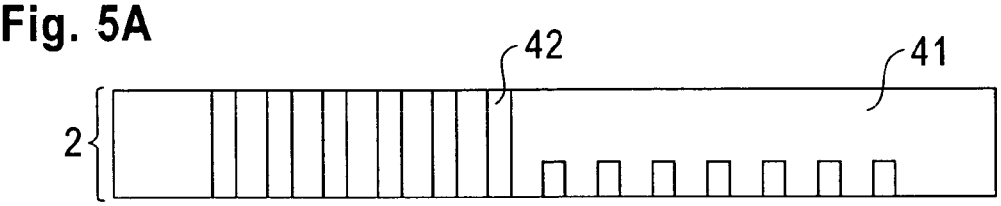
Figure 5B:
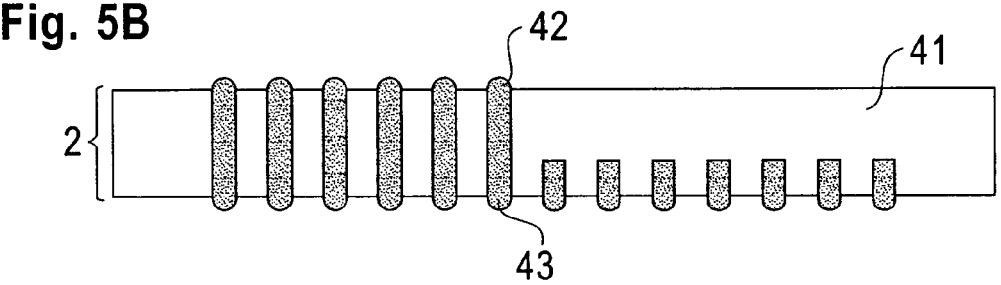
Figure 5C:
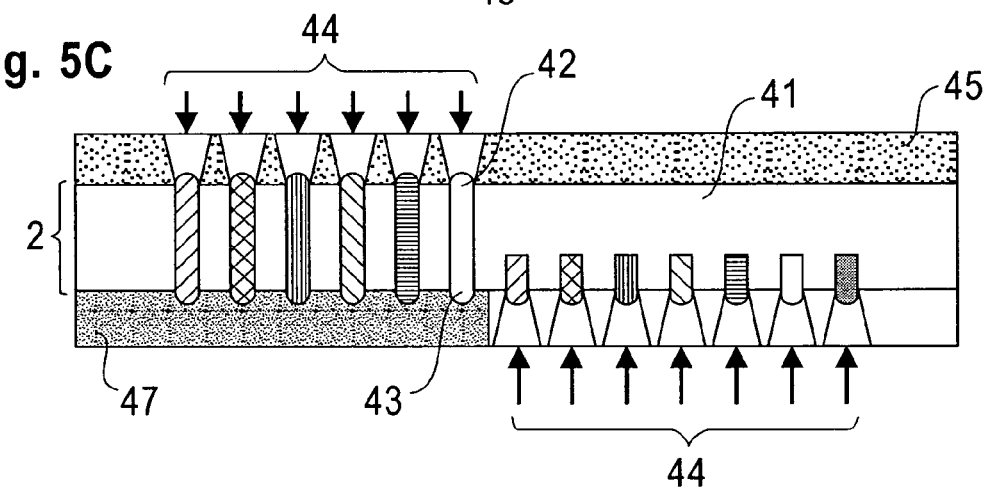
Figure 5D:
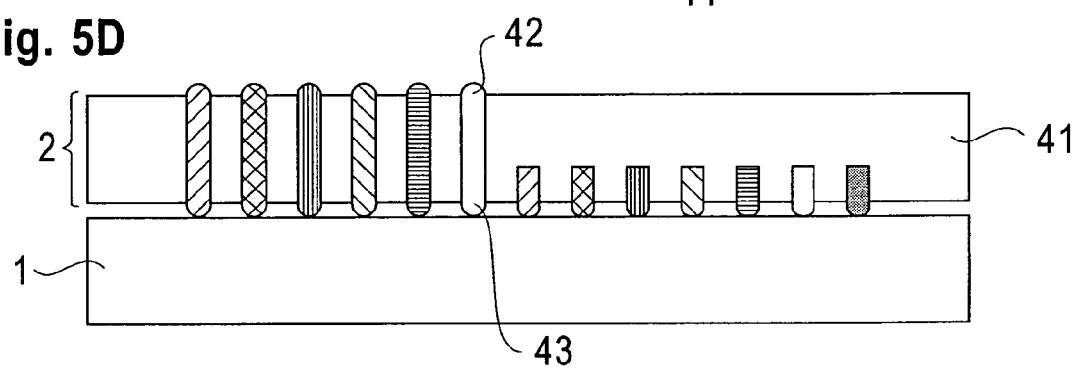
Figure 5E:
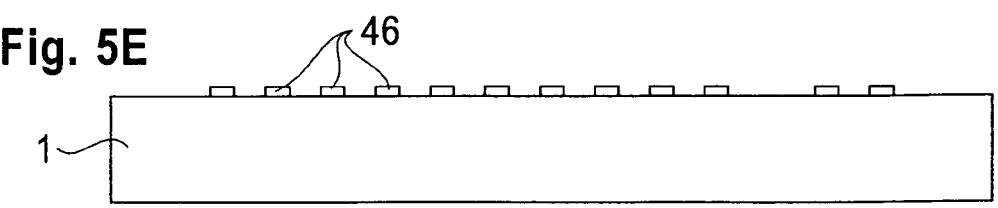

In a modification of the PCR technique herein before described, linear amplification of DNA can be achieved by applying antisense DNA primers in solution. This modification will now be described with reference to FIGS. 4A to 4E. Referring to FIG. 4A, template oligomers 8 are initially held on the stamp 2 by capture oligomers 7. The stamp 2 is then brought into contact with the surface with the first primers 9 only are immobilized. A fraction of the templates 8 hybridize with the immobilized primers 9 and are thus transferred from the stamp 2 to the surface 1. Turning to FIG. 4B, a PCR mix 11 comprising DNA polymerase and the four PCR nucleotides (dNTPs) in a buffer solution of phosphate buffered saline (PBS) is then added. Each immobilized primer hybridized to a DNA template is amplified by the PCR mix 11 to full length on the surface 1. This produces a synthesized complementary or duplex DNA strand. Referring now to FIG. 4C, the second primer 12 is added in solution and heat applied. The synthesized strand is melted and rehybridized. Referring to FIG. 4D, a second generation complementary strand is then synthesized. Referring to FIG. 4E, the synthesis is repeated, until all oligomers are extended. This method is preferable performed in a sealed container to avoid cross contamination of the generated and detached template strands.

In preferred embodiments of the present invention, a fraction or catalytic amount of molecules is transferred from a stamp 2 to the surface 1 via mechanical contact with the surface 1 in a dry or wet state. This is achieved by the molecules to be transferred having a stronger bond to the stamp 2 than to the surface 1.

It is desirable to employ a controllable chemisorption protocol that deters nonspecific adsorption on the surface 1 or on the stamp 2. An example of such a reaction involves preparation of a heterobifunctional reagent such as NHS-PEG-triethoxysilane from APTS and a homobifunctional PEG such as (a,w) NHS-PEG 2000, Rapp Polymere which is exposed to a glass surface by filling a gap between glass slides at elevated temperature. Chemisorption may be performed by filling PDMS microfluidic systems applied to the NHS-activated surface with aqueous solutions of amino-functionalized oligomers.

PCR amplification can be performed using two surface bound primers as herein before described with reference to FIG. 3, or using one surface bound primer and one soluble primer as herein before described with reference to FIG. 4. However, in the latter case, traces of intermediate templates can diffuse away from their synthesis location and diffuse into adjacent areas. It is therefore desirable to confine soluble primer based PCR amplification. For biosensor applications, only one sense strand and not the antisense strand should be present on the surface 1. The other strand is therefore preferably either cleaved from the surface or stopped from chemically attaching by use of, for example, soluble primers.

Referring back to FIG. 1, as indicated earlier, active zones 5,6 of the stamp 2 are selectively coated in a preferred embodiment of the present invention with a capture molecule and an inking molecule such as a template strand. Such selective coating may be performed via a range of different methods, including: pipetting; capillary printing; ink jet; and, pin spotting, as herein before described. Other coating techniques, such as application of ink via a microfluidic network or via a stencil with selective openings are equally possible. A topographically patterned stamp usually produces a more accurate pattern than a flat stamp patterned with ink. This is because the active zones 5,6 are topographically separated. The delimitation is effective both when active zones 5,6 are protruding and when they are recessed.

Referring now to FIG. 5, in a particularly preferred embodiment of the present invention, the stamp 2 comprises a body 41 having plurality of active zones in the form of pores 42. The pores 42 may be open to each end or closed at one end. Referring to FIG. 5B, each pore 42 is filled with a hydrophilic polymer gel matrix 43. Referring to FIG. 5C, each pore 42 may be filled with molecules 44 of different species. A stencil 45 or microfluidic network may be employed to mask each pore 42 from the other pores during filling, thus preventing cross contamination of the pores 42. The filling may be by diffusion or by an electric field. Referring to FIG. 5D, in operation, the stamp 2 contacts the surface 1. Molecules are printed on the surface 1 from the gel in the pores 42. Referring to FIG. 5E, printed areas 46 of molecules are left on the surface 1.

In a particularly preferred embodiment of the present invention, the pores 42 are each loaded with a different species of template DNA. By uptake of water 47 or buffer, the gel 43 swells to its equilibrium in a 100% humidity environment. The gel 43 thus protrudes beyond the stamp surface. The stamp 2 may be stored in a humid environment to prevent the subsequent drying of the gel 42. With a loading of around 1 W % DNA in the gel, millions of surfaces may be printed from the same stamp 2 with a catalytic amount of DNA transferred each time. Subsequent amplification of the catalytic seed layers can be employed to complete the DNA monolayers. Refilling of the stamp 2 need be performed only when the stamp 2 is no longer able to transfer a seed layer. To deposit the seed layers, the stamp 2 is brought into contact with the surface 1 to transfer the desired amount of seed molecules. The stamp 2 need not be immersed in liquid, thereby reducing printing complexity. The gel 43 permits full hydration of molecules thus enhancing chemisorption of the molecules to the surface 1. The gel 43 is permeable, thus allowing trapped water to escape. This avoids separation of the printing surfaces in the presence of a third medium. DNA may be held on the surface of a pore 42 rather than within the gel 43. Here, it is desirable to effect contact between the stamp 2 and the surface 1 in a third medium with the pores 42 isolated from each other. After contact, the temperature can be increased to promote the dissociation of traces of template DNA strands from the stamp 2 and deposition on the surface 1.

In a preferred embodiment of the present invention, the active zones 5,6 of the stamp 2 herein before described with reference to FIG. 1 are each provided with oligomer for capturing template DNA strands. The DNA strands are then exposed to the surface 1 such that only a small fraction, typically <0.1% of a monolayer of DNA strands are transferred. This is achieved by providing hybridizing anchors with shorter length on the surface 1. The number of DNA strands transferred may be around 25 per square micrometer with a transfer efficiency of 0.1% and a DNA diameter of 2 nm. The stamp 2 can thus be used for several hundred printing operations before reinking is needed. The density of DNA strands on the surface is then brought to saturation via the herein before described PCR amplification scheme involving surface bound primers. The active zones 5,6 on the stamp 2 may range from microns to millimeters in size.

Patterning of templates for PCR onto the primer may also be achieved by microfluidic networks. Use of solutions with low concentration of templates and conditions unfavorable to fast binding of templates to the surface permit conservation of templates and patterning of homogeneous areas on the surface. Replication can also be applied to repair of defects in printed monolayer and to situations where an autocatalytic center is printed and a catalytic reaction is started.

The invention claimed is:

1. A method for producing a monolayer of molecules on a surface, the method comprising:
    loading a stamp with seed molecules;
    transferring seed molecules from the stamp to a flat surface, wherein the transferring comprises transferring a fraction of the seed molecules loaded on the stamp to the flat surface and wherein the transferring comprises adsorbing the seed molecules to the stamp and adsorbing the seed molecules to the flat surface, the adsorption of the seed molecules to the stamp being stronger than the adsorption of the seed molecules to the flat surface; and
    self-completing amplification of the seed molecules via an amplifying reaction to produce the monolayer on the flat surface, wherein self-completing amplification of the seed molecules via an amplifying reaction to produce the monolayer comprises producing a homogeneous area, wherein the homogeneous area comprises a monolayer of molecules on the flat surface, and wherein the monolayer of molecules on the flat surface has no diffusive seed molecules that can relocate and destroy amplification accuracy.

2. A method as claimed in claim 1, wherein the amplifying comprises linear amplification of the seed molecules.

3. A method as claimed in claim 1, wherein the amplifying comprises exponential amplification of the seed molecules.

4. A method as claimed in claim 1, wherein the amplifying comprises directional amplification of the seed molecules.

5. A method as claimed in claim 4, wherein the seed molecules are directionally amplified to form conductive structures.

6. A method as claimed in claim 4, comprising electroless plating of the directionally amplified seed molecules with a metal.

7. A method as claimed in claim 4, wherein the directional amplification is controlled by the geometry of the seed molecule.

8. A method as claimed in claim 4, wherein the directional amplification is controlled by application of an external force.

9. A method as claimed in claim 8, wherein the external force comprises an electrical force.

10. A method as claimed in claim 8, wherein the external force comprises a magnetic force.

11. A method as claimed in claim 8, wherein the external force comprises a hydrodynamic force.

12. A method as claimed in claim 1, wherein the amplifying comprises a polymerase chain reaction.

13. A method as claimed in claim 1, wherein the amplifying comprises the use of an in vitro translation system to produce a monolayer of protein.

14. A method as claimed in claim 1, wherein the monolayer protects the surface from etchants.

15. A method as claimed in claim 1, wherein the monolayer comprises DNA.

16. A method as claimed in claim 1, comprising repeating the transferring and amplifying on plural surfaces before reloading the stamp with seed molecules.

* * * * *